US006624328B1

(12) United States Patent  
Guerra

(10) Patent No.: US 6,624,328 B1
(45) Date of Patent: Sep. 23, 2003

(54) PREPARATION OF PERFLUORINATED VINYL ETHERS HAVING A SULFONYL FLUORIDE END-GROUP

(75) Inventor: Miguel Antonio Guerra, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/322,226

(22) Filed: Dec. 17, 2002

(51) Int. Cl.$^7$ ............................................. C07C 309/00
(52) U.S. Cl. ................. 562/825; 204/157.78; 204/157.8
(58) Field of Search ................. 562/821, 824, 562/825; 568/28, 35; 204/157.6, 157.76, 157.78, 157.8

(56) References Cited

U.S. PATENT DOCUMENTS

| | | | |
|---|---|---|---|
| 2,732,398 A | 1/1956 | Brice et al. | |
| 3,114,778 A | 12/1963 | Gerhard et al. | |
| 3,250,608 A | 5/1966 | Griffith | |
| 3,250,808 A | 5/1966 | Moore, Jr. et al. | |
| 3,282,875 A | 11/1966 | Connolly et al. | |
| 3,291,843 A | 12/1966 | Fritz et al. | |
| 3,301,893 A | 1/1967 | Putnam et al. | |
| 3,311,658 A | 3/1967 | Warnell | |
| 3,450,684 A * | 6/1969 | Darthy | 526/247 |
| 3,560,568 A * | 2/1971 | Resnick | 562/111 |
| 4,329,434 A | 5/1982 | Kimoto et al. | |
| 4,329,435 A | 5/1982 | Kimoto et al. | |
| 4,330,654 A | 5/1982 | Ezzell et al. | |
| 4,332,954 A | 6/1982 | Koshar | |
| 4,337,137 A | 6/1982 | Ezzell | |
| 4,340,750 A * | 7/1982 | Yamabe et al. | 560/183 |
| 4,358,412 A | 11/1982 | Ezzell et al. | |
| 4,358,545 A | 11/1982 | Ezzell et al. | |
| 4,417,969 A | 11/1983 | Ezzell et al. | |
| 4,425,199 A | 1/1984 | Hamada et al. | |
| 4,466,881 A | 8/1984 | Hamada et al. | |
| 4,510,328 A | 4/1985 | Kimoto et al. | |
| 4,511,518 A | 4/1985 | Kimoto et al. | |
| 4,536,352 A | 8/1985 | Kimoto et al. | |
| 4,554,112 A * | 11/1985 | Ezzell et al. | 562/825 |
| 4,555,369 A | 11/1985 | Kimoto et al. | |
| 4,597,913 A | 7/1986 | Kimoto et al. | |
| 4,613,467 A | 9/1986 | Kimoto et al. | |
| 4,749,526 A | 6/1988 | Flynn | |
| 4,834,922 A * | 5/1989 | Ezzell et al. | 558/449 |
| 4,997,988 A * | 3/1991 | Roberts et al. | 568/50 |
| 5,103,051 A * | 4/1992 | Navarrini et al. | 562/825 |
| 5,241,110 A * | 8/1993 | Navarrini et al. | 562/111 |
| 5,318,674 A * | 6/1994 | Behr et al. | 205/430 |
| 5,902,908 A | 5/1999 | Morita et al. | |
| 6,255,536 B1 | 7/2001 | Worm et al. | |
| 6,388,139 B1 * | 5/2002 | Resnick | 568/32 |

FOREIGN PATENT DOCUMENTS

JP 58-93728 6/1983

* cited by examiner

Primary Examiner—Jean F. Vollano
(74) Attorney, Agent, or Firm—Philip Y. Dahl

(57) ABSTRACT

A method is provided for making a perfluorinated vinyl ether having a sulfonyl fluoride end-group according to the formula $FSO_2-(CF_2)_n-O-CF=CF_2$, where n is 2–5, comprising the steps of: a) fluorination of:

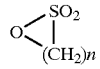

to produce $FSO_2-(CF_2)_{(n-1)}-COF$; b) reaction of $FSO_2-(CF_2)_{(n-1)}-COF$ with hexafluoropropylene oxide (HFPO) to produce $FSO_2-(CF_2)_{(n)}-O-CF(CF_3)-COF$; c) reaction of $FSO_2-(CF_2)_{(n)}-O-CF(CF_3)-COF$ with a salt of a metal cation $M+P$, where p is the valence of M, to produce $(FSO_2-(CF_2)_{(n)}-O-CF(CF_3)-COO^-)_p M+P$; and d) thermal cracking of $FSO_2-(CF_2)_{(n)}-O-CF(CF_3)-COO^-)_p M+P$ to produce $FSO_2-(CF_2)_{(n)}-O-CF=CF_2$.

17 Claims, No Drawings

PREPARATION OF PERFLUORINATED VINYL ETHERS HAVING A SULFONYL FLUORIDE END-GROUP

FIELD OF THE INVENTION

This invention relates to a four-step method for preparation of perfluorinated vinyl ethers having sulfonyl fluoride end-groups according to the formula $FSO_2-(CF_2)_n-O-CF=CF_2$, where n is 2–5, which are an important class of monomers in the synthesis of ion exchange resins.

BACKGROUND OF THE INVENTION

U.S. Pat. No. 4,749,526 discloses preparations for fluoroaliphatic ether-containing carbonyl fluoride compounds by reacting a fluorinated carbonyl compound with hexafluoropropylene oxide in the presence of at least one catalyst selected from potassium iodide, potassium bromide, cesium iodide, cesium bromide, rubidium iodide and rubidium bromide.

U.S. Pat. No. 5,902,908 discloses a method for preparing a fluorinated vinyl ether by reacting a fluorinated carboxylic acid halogenide with a metal compound below the decomposition temperature for the corresponding metal salt in the absence of solvent and then raising the temperature of the produced corresponding metal salt above the decomposition temperature.

U.S. Pat. No. 6,255,536, incorporated herein by reference, discloses a process for the preparation of a perfluorinated vinyl ether of the formula $CF_2=CF-O-R_f$ wherein $R_f$ is a linear, branched or cyclic perfluorinated aliphatic group that may contain oxygen atoms hereby forming additional ether linkages.

SUMMARY OF THE INVENTION

Briefly, the present invention provides a method of making a perfluorinated vinyl ether having a sulfonyl fluoride end-group according to the formula $FSO_2-(CF_2)_n-O-CF=CF_2$, where n is 2–5, comprising the steps of: a) fluorination of:

to produce $FSO_2-(CF_2)_{(n-1)}-COF$; b) reaction of $FSO_2-(CF_2)_{(n-1)}-COF$ with hexafluoropropylene oxide (HFPO) to produce $FSO_2-(CF_2)_{(n)}-O-CF(CF_3)-COF$; c) reaction of $FSO_2-(CF_2)_{(n)}-O-CF(CF_3)-COF$ with a salt of a metal cation M+P, where p is the valence of M, to produce $(FSO_2-(CF_2)_{(n)}-O-CF(CF_3)-COO^-)_pM+P$; and d) thermal cracking of $FSO_2-(CF_2)_{(n)}-O-CF(CF_3)-COO^-)_pM+P$ to produce $FSO_2-(CF_2)_{(n)}-O-CF=CF_2$.

It is an advantage of the present invention to provide a convenient and efficient method for preparation of perfluorinated vinyl ethers having sulfonyl fluoride end-groups according to the formula $FSO_2-(CF_2)_n-O-CF=CF_2$, which uniquely adapted to the case where n is 2–5, and especially the case where n is 4, these species being important monomers in the synthesis of ion exchange resins. It is a further advantage of the present invention to provide a method for preparation of perfluorinated vinyl ethers having sulfonyl fluoride end-groups according to the formula $FSO_2-(CF_2)_n-O-CF=CF_2$, where n is 2–5, which does not require the use of tetrafluoroethylene (TFE), with it's associated hazards and difficulty.

DETAILED DESCRIPTION OF PREFERRED EMBODIMENTS

Briefly, the present invention provides a method of making a perfluorinated vinyl ether having a sulfonyl fluoride end-group according to the formula $FSO_2-(CF_2)_n-O-CF=CF_2$, where n is 2–5, comprising the steps of: a) fluorination of:

to produce $FSO_2-(CF_2)_{(n-1)}-COF$; b) reaction of $FSO_2-(CF_2)_{(n-1)}-COF$ with hexafluoropropylene oxide (HFPO) to produce $FSO_2-(CF_2)_{(n)}-O-CF(CF_3)-COF$; c) reaction of $FSO_2-(CF_2)_{(n)}-O-CF(CF_3)-COF$ with a salt of a metal cation M+P, where p is the valence of M, to produce $(FSO_2-(CF_2)_{(n)}-O-CF(CF_3)-COO^-)_pM+P$; and d) thermal cracking of $FSO_2-(CF_2)_{(n)}-O-CF(CF_3)-COO^-)_pM+P$ to produce $FSO_2-(CF_2)_{(n)}-O-CF=CF_2$. The value of n is 2–5, typically 3–4, and most typically 4. The value of p is typically 1 or 2, and most typically 1. The salt of a metal cation M+P is most typically $Na_2CO_3$.

Step a) involves fluorination of a sultone, which is a 4–7 member ring according to the formula:

where n is 2–5, to produce $FSO_2-(CF_2)_{(n-1)}-COF$. Fluorination may be accomplished by any suitable means, but is most typically accomplished by electrochemical fluorination as described in U.S. Pat. No. 2,732,398, incorporated herein by reference.

Step b) involves reaction of $FSO_2-(CF_2)_{(n-1)}-COF$ with hexafluoropropylene oxide (HFPO) to produce $FSO_2-(CF_2)_{(n)}-O-CF(CF_3)-COF$. Step b) may be accomplished by any suitable means, but is typically accomplished by addition of HFPO to a solution of $FSO_2-(CF_2)_{(n-1)}-COF$ in a suitable polar solvent such diglyme. Typically, a catalyst is present. The catalyst is typically a fluoride catalyst, most typically KF. The reaction may be performed in the absence of any catalyst other than a fluoride catalyst. Typically, HFPO is added in a molar amount that does not exceed the molar amount of $FSO_2-(CF_2)_{(n-1)}-COF$ present. More typically, the molar amount of $FSO_2-(CF_2)_{(n-1)}-COF$ present remains in excess of the molar amount of HFPO present by at least 10%, more typically 20%, and more typically 30%. Step b) may be accomplished by methods disclosed in copending U.S. patent application Ser. No. 10/322,254, filed on even date herewith, incorporated herein by reference.

Step c) involves reaction of $FSO_2-(CF_2)_{(n)}-O-CF(CF_3)-COF$ with a salt of a metal cation M+P, where p is the valence of M, to produce $(FSO_2-(CF_2)_{(n)}-O-CF(CF_3)-COO^-)_pM+P$. The valence p may be any valence but is typically 1 or 2 and most typically 1. M may be any suitable metal, but is typically selected from Na, K, Rb and Cs and is most typically Na. The anion of the salt is any suitable anion, but typically one that is not so basic as to remove the fluorine from the sulfonyl fluoride function. The salt of a metal cation M+P is most typically $Na_2CO_3$. Step c) is typically carried out in a polar solvent, such as glyme, diglyme, and the like. Step c) is typically carried out at elevated temperature, typically between 40 and 100° C.

Step d) involves thermal cracking of $(FSO_2-(CF_2)_{(n)}-O-CF(CF_3)-COO^-)_pM+P$ to produce $FSO_2-(CF_2)_{(n)}-$ O—CF=CF$_2$, after removal of solvent. Any heat source sufficient to raise the temperature of produce (FSO$_2$—(CF$_2$)$_{(n)}$—O—CF(CF$_3$)—COO$^-$)$_p$M+P to its decomposition temperature may be used. Decomposition temperatures vary with reactants, but will typically fall between 160° C. and 210° C. Typically, any remaining solvent is removed prior to thermal cracking, typically by application of vacuum or reduced pressure. The product may then be collected, isolated and purified by any suitable means.

It will be appreciated that isolation and purification of reaction products may be desirable following one or more of the steps of the present method.

This invention is useful in the synthesis of perfluorinated vinyl ethers having sulfonyl fluoride end-groups, which are an important class of monomers in the synthesis of ion exchange resins.

Objects and advantages of this invention are further illustrated by the following examples, but the particular materials and amounts thereof recited in these examples, as well as other conditions and details, should not be construed to unduly limit this invention.

EXAMPLE

Unless otherwise noted, all reagents were obtained or are available from Aldrich Chemical Co., Milwaukee, Wis., or may be synthesized by known methods.

A.

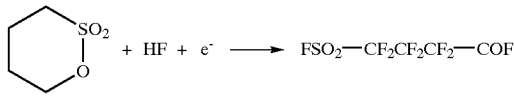

1,4-Butane sultone (6900 g, 50.7 m) was electrochemically fluorinated in HF as described in U.S. Pat. No. 2,732,398 to give 4-(fluorosulfonyl)hexafluorobutyryl fluoride, FSO$_2$(CF$_2$)$_3$COF (4000 g, 14.3 m for a 28% yield).

FSO$_2$—CF$_2$CF$_2$CF$_2$—COF+CF$_3$CFOCF$_2$+KF→FSO$_2$—CF$_2$CF$_2$CF$_2$CF$_2$—O—CF(CF$_3$)—COF     B.

2162 g (7.7 m) of 4-(fluorosulfonyl) hexafluorobutyryl fluoride, FSO$_2$(CF$_2$)$_3$COF, was reacted with an equimolar amount of hexafluoropropylene oxide (HFPO) (1281 g, 7.7 m) in 2L diglyme with 114 g potassium fluoride to give perfluoro-4-(fluorosulfonyl) butoxypropionyl fluoride (2250 g, 5.1 m for a 65% yield) and 675 g of a higher boiling byproduct that had an additional hexafluoropropylene oxide unit.

FSO$_2$—CF$_2$CF$_2$CF$_2$CF$_2$—O—CF(CF$_3$)—COF+Na$_2$CO$_3$+heat→
FSO$_2$—CF$_2$CF$_2$CF$_2$CF$_2$—O—CF=CF$_2$     C.

1108 g (2.5 m) of perfluoro-4-(fluorosulfonyl) butoxypropionyl fluoride was then reacted with sodium carbonate (603 g, 5.7 m) in glyme at 70° C. to make the sodium salt of the acid. Solvent was then removed under vacuum and the dried salt was heated to 165° C. to break vacuum with the carbon dioxide byproduct and continuing to heat up to 182° C. to isolate perfluoro-4-(fluorosulfonyl)butoxyvinyl ether (703 g, 1.9 m for a 74% yield).

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

I claim:

1. A method of making a perfluorinated vinyl ether having a sulfonyl fluoride end-group according to the formula FSO$_2$—(CF$_2$)$_n$—O—CF=CF$_2$, where n is 2–5, comprising the steps of:

a) fluorination of:

to produce FSO$_2$—(CF$_2$)$_{(n-1)}$—COF;

b) reaction of FSO$_2$—(CF$_2$)$_{(n-1)}$—COF with hexafluoropropylene oxide (HFPO) to produce FSO$_2$—(CF$_2$)$_{(n)}$—O—CF(CF$_3$)—COF;

c) reaction of FSO$_2$—(CF$_2$)$_{(n)}$—O—CF(CF$_3$)—COF with a salt of a metal cation M+P, where p is the valence of M, to produce (FSO$_2$—(CF$_2$)$_{(n)}$—O—CF(CF$_3$)—COO$^-$)$_p$M+P; and d) thermal cracking of FSO$_2$—(CF$_2$)$_{(n)}$—O—CF(CF$_3$)—COO$^-$)$_p$M+P to produce FSO$_2$—(CF$_2$)$_{(n)}$—O—CF=CF$_2$.

2. The method according to claim 1 wherein n=4.

3. The method according to claim 1 wherein step c) is performed in a polar solvent.

4. The method according to claim 1 wherein said salt of a metal cation is Na$_2$CO$_3$.

5. The method according to claim 3 wherein said salt of a metal cation is Na$_2$CO$_3$.

6. The method according to claim 1 wherein said step b) is performed in the presence of a fluoride catalyst.

7. The method according to claim 6 wherein said step b) is performed in the absence of any catalyst other than a fluoride catalyst.

8. The method according to claim 6 wherein said fluoride catalyst is KF.

9. The method according to claim 7 wherein said fluoride catalyst is KF.

10. The method according to claim 1 wherein, throughout said step b), the molar amount of FSO$_2$—(CF$_2$)$_{(n-1)}$—COF present remains in excess of the molar amount of HFPO present by at least 10%.

11. The method according to claim 6 wherein, throughout said step b), the molar amount of FSO$_2$—(CF$_2$)$_{(n-1)}$—COF present remains in excess of the molar amount of HFPO present by at least 10%.

12. The method according to claim 1 wherein said step a) comprises electrochemical fluorination.

13. The method according to claim 2 wherein said step a) comprises electrochemical fluorination.

14. The method according to claim 5 wherein said step a) comprises electrochemical fluorination.

15. The method according to claim 6 wherein said step a) comprises electrochemical fluorination.

16. The method according to claim 10 wherein said step a) comprises electrochemical fluorination.

17. The method according to claim 11 wherein said step a) comprises electrochemical fluorination.

* * * * *

UNITED STATES PATENT AND TRADEMARK OFFICE
CERTIFICATE OF CORRECTION

PATENT NO. : 6,624,328 B1
DATED : September 23, 2003
INVENTOR(S) : Guerra, Miguel A.

It is certified that error appears in the above-identified patent and that said Letters Patent is hereby corrected as shown below:

Title page,
Item [56], References Cited, U.S. PATENT DOCUMENTS; "Darthy" should be -- Darby --.
Item [57], ABSTRACT
Line 14, "cation M + P" should be -- cation $M^{+p}$ --.
Line 15, "M + P; and" should be -- $M^{+p}$; and --.
Line 17, "M + P to" should be -- $M^{+p}$ to --.

Column 1,
Line 51, "cation M + P" should be -- cation $M^{+p}$ --.
Line 52, "M + P; and" should be -- $M^{+p}$; and --.
Line 53, "M + P to" should be -- $M^{+p}$ to --.
Line 59; "which uniquely" should be -- which is uniquely --.

Column 2,
Line 17, "cation M+ P" should be -- cation $M^{+p}$ --.
Line 18, "M + P; and" should be -- $M^{+p}$; and --.
Line 20, "M + P to" should be -- $M^{+p}$; and --.
Line 23, "cation M + P" should be -- cation $M^{+p}$ --.
Line 24, "sultone" should be -- sulfone --.
Line 40, "such diglyme." should be -- such as diglyme. --.
Line 54, "cation M + P" should be -- $M^{+p}$ --.
Line 56, "M + P" should be -- $M^{+p}$ --.
Line 62, "cation M + P" should be -- cation $M^{+p}$ --.
Line 67, "M + P" should be -- $M^{+p}$ --.

Column 3,
Line 2, delete "produce".
Line 3, "M + P" should be -- $M^{+p}$ --.
Line 35, "sultone" should be -- sulfone --.

UNITED STATES PATENT AND TRADEMARK OFFICE
CERTIFICATE OF CORRECTION

PATENT NO.    : 6,624,328 B1
DATED         : September 23, 2003
INVENTOR(S)   : Guerra, Miguel A.

It is certified that error appears in the above-identified patent and that said Letters Patent is hereby corrected as shown below:

Column 4,
Line 20, "$(_{n-1})$" should be -- $_{(n-1)}$ --.
Line 24, "cation M + P" should be -- cation $M^{+p}$ --
Line 26, "M + P" should be -- $M^{+p}$ --.
Line 28, "M + P" should be -- $M^{+p}$ --.

Signed and Sealed this

First Day of June, 2004

JON W. DUDAS
*Acting Director of the United States Patent and Trademark Office*